United States Patent [19]

Jones et al.

[11] 4,428,392

[45] Jan. 31, 1984

[54] BREATHING VALVE

[75] Inventors: Leon Jones, Huntington Beach; Orland W. Wilcox, Pasadena, both of Calif.

[73] Assignee: Protection, Inc., Pomona, Calif.

[21] Appl. No.: 334,263

[22] Filed: Dec. 24, 1981

[51] Int. Cl.³ .......................... A62B 9/02; F16K 7/18
[52] U.S. Cl. ............................ 137/102; 137/512.15; 137/854; 137/859; 251/DIG. 2; 128/205.24
[58] Field of Search ............... 137/102, DIG. 9, 859, 137/512.2; 128/205.13, 205.16, 205.24; 251/DIG. 2, 61.1, 331

[56] References Cited

U.S. PATENT DOCUMENTS

| 3,282,288 | 11/1966 | Sheppard | 251/331 |
| 3,342,200 | 9/1967 | Wilcox | 137/102 |
| 4,172,465 | 10/1979 | Dashner | 137/543.15 |

*Primary Examiner*—Martin P. Schwadron
*Assistant Examiner*—James R. Shay
*Attorney, Agent, or Firm*—Donald D. Mon

[57] ABSTRACT

A breathing valve for the selective entry of a gas to be inhaled and for the exit of exhaled gas, which utilizes a rolling diaphragm and flapper valves for its workings which are quiet and are constructed so as to be unlikely to freeze up or become sticky.

15 Claims, 3 Drawing Figures

BREATHING VALVE

FIELD OF THE INVENTION

This invention relates to breathing valves for use in systems which supply gas to a user such as to his gas mask, and permit the exhaust of exhaled gases.

BACKGROUND OF THE INVENTION

Breathing valves which interconnect a using device such as a gas mask to a source of gas to be breathed and then exhausted to atmosphere are known. For example, see Orland W. Wilcox U.S. Pat. No. 3,342,200, issued Sept. 19, 1967.

Such valves are frequently used under pressure strenuous and extreme conditions such as by miners and by firemen, as well as by pilots, and can become fouled with saliva and condensed moisture from the man's breath. Especially under cold ambient conditions, valves which utilize sliding and abutting valve workings can freeze up and stick. Also, when they dry out, they can become sticky. These of course are intolerable situations where a man's life may depend upon his ability freely to inhale and exhale.

Furthermore, it is commonly recognized that such valves ought to be quieter than they conventionally are. Especially when the person is working in quiet surroundings where his attention should not be distracted, clicks which occur whenever he inhales or exhales are very distracting, especially when he is using a microphone.

Accordingly it is an object of this invention to provide a breathing valve which is unlikely to stick even under most and cold conditions, and which operates reliably and silently.

BRIEF DESCRIPTION OF THE INVENTION

A breathing valve according to this invention has a body with a cavity therein. There is an inlet port leading to the cavity adapted to be connected to a source of gas. There is connector port adapted to be connected to a using device such as a hose leading to a mask or even directly to the mask itself. The body has a peripheral wall with an inner surface and an outer surface, and at least one exit port interconnecting the surfaces. A rolling diaphragm is mounted to a central piston which diaphragm rolls over the exit port to cover it, or can be unrolled to uncover the port, both as a function of piston movement. The piston has at least one passage within a seat to enable gas to pass from the inlet port into the cavity toward the connector port, and a flapper valve is carried by the piston adapted to overlay the passage so as to control unidirectional flow of gas therethrough. An outlet check valve overlays the exit port at the outer surface of the peripheral wall so as to permit only unidirectional flow of gas from the cavity to the exterior of the valve. The piston is shifted as a consequence of the user's breathing. When he inhales, the piston is shifted in a direction which causes the rolling diaphragm to close the exit port, and the intake flapper valve to open and admit breathing gas. When the user exhales, the pressure moves the piston against a bias means to close the inlet flapper valve and roll the diaphragm away from the exit port, to permit exit of gases through the outlet check valve.

According to a preferred but optional feature of this invention, the rolling diaphragm, the flapper valve and the outlet check valve are made of silicone rubber.

The above and other features of this invention will be fully understood from the following detailed description and the accompanying drawings, in which:

DETAILED DESCRIPTION OF THE INVENTION

Figure 1:
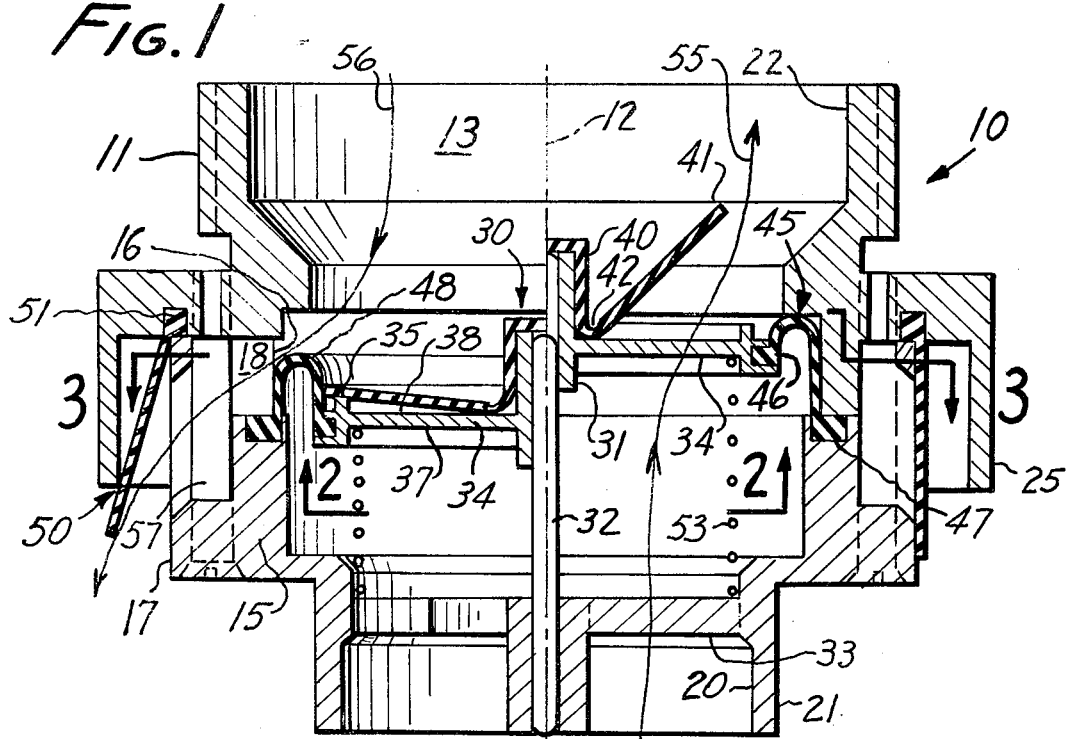
FIG. 1 is an axial cross-section of the presently preferred embodiment of the invention, shown both in the inhaling condition and in the exhaling conditon.

The presently preferred embodiment of a breathing valve 10 according to the invention is shown in FIG. 1. It will be observed that the left hand section shows the valve in one operating position (exhale) and the right hand portion shown a different one (inhale). Of course the part is unitary and is not split.

Figure 3:
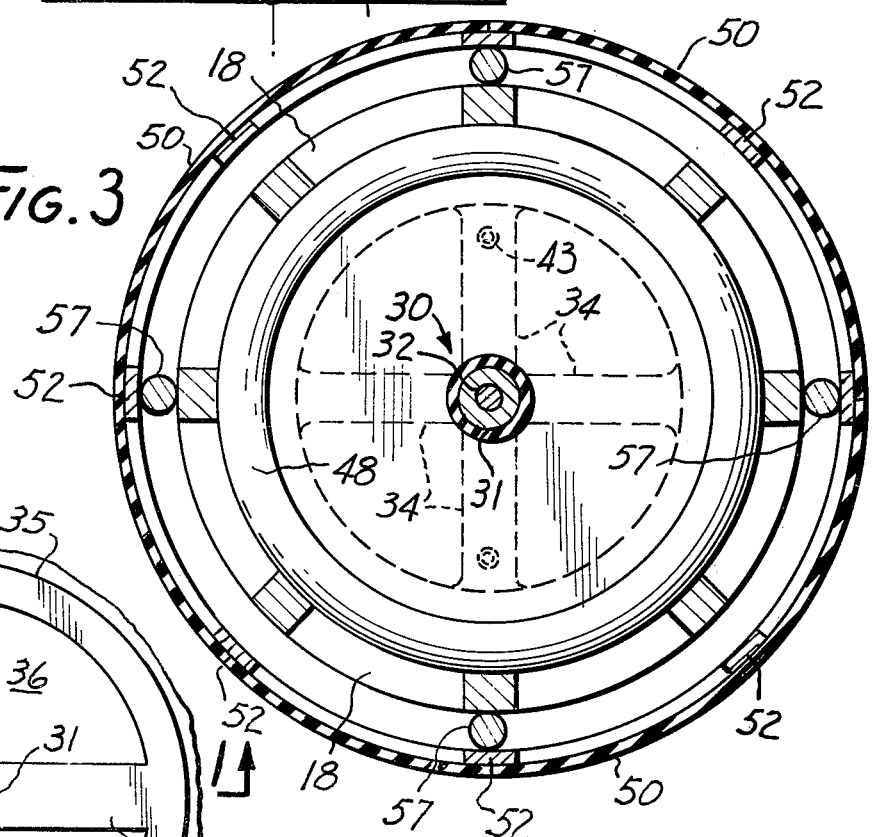
FIGS. 2 and 3 are fragmentary cross-sections taken respectively at lines 2—2 and 3—3 in FIG. 1.
Figure 2:
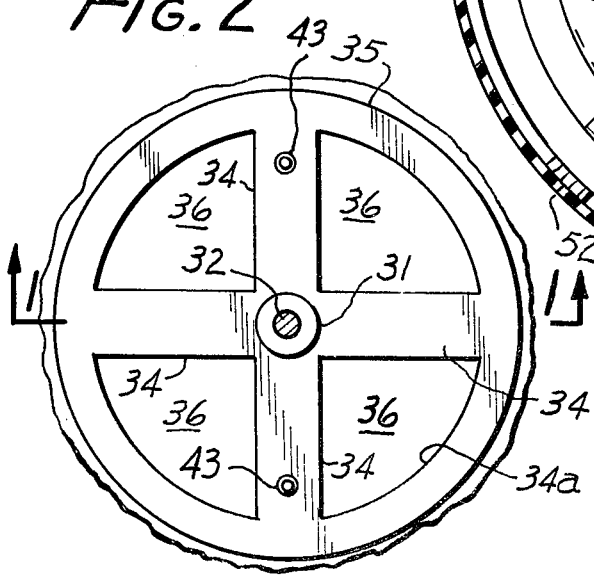

The valve includes a body 11 which has an axis 12 and an internal cavity 13. A peripheral wall 15 has an annular inner surface 16 and an outer surface 17 which also is preferably annular. At least the inner surface has its center of curvature on axis 12. The peripheral wall 15 has at least one, and preferably a plurality of, exit ports 18. As best shown in FIG. 3, these exit ports are spaced-apart from one another by portions of both the outer surface and the inner surface for sealing purposes. The outer opening of exit ports 18 is larger than the inner opening.

Body 11 also has an inlet port 20 adapted to be connected to a source of breathing gas such as by a hose fitted over neck 21. The inlet port enters the cavity. A connector port 22 also opens into the cavity and is adapted to be connected to a using device such as a hose leading to a mask, or to the mask itself.

The body has a peripheral skirt 25 overhanging at least a major portion of the exit ports for mechanical protective purposes.

A piston 30 is movably mounted in a cavity, and is centered on the axis. It includes a central spindle 31 that is slidably mounted on a central shaft 32, the shaft projecting into the cavity from a spider 33 in the inlet port. It will be recognized that the piston is shown in two different positions in FIG. 1, but it will be understood that it is a single piece, the two positions being shown in the same Figure for convenience in description of the operation of the breathing valve.

A plurality of spokes 34 extends from the spindle 31 to a rim 34a. The rim bears a seat 35 that encircles the axis. The spokes are spaced apart from one another, and form between them at least one, and preferably a plurality, of passages 36 which extend from a first face 37 of the piston facing toward the inlet port to a second face 38 which is communicable with the connector port.

An inlet flapper valve 40 is mounted to the spindle by a central neck-like portion thereof. It extends as a continuous disc 41 out to the seat and it is adapted to overlay and contact the seat so as to close the passages in the exhale (left hand) condition and to move away therefrom in the inhaling operation. Preferably this valve is provided as a continuous disc and relies on flexibility and elasticity of the material to move away from the seat. Individual flapper leaflets are provided which can bend at an edge 42 to rise (right hand part of FIG. 1) to pass air and lower (left hand part of FIG. 1) to seal with seat 35. The illustrated arrangement has the advantage of simplicity of parts, and reliability in operation.

Flapper valve 40 is held to a pair of spokes 34 by elastic, flexible nibs 43 that pass through holes in the spokes, and have enlargements that engage the reverse side of the spokes.

A peripheral rolling diaphragm 45 has an inner edge 46, an outer edge 47, and a flexible imperforate web 48 interconnecting them. The inner edge is mounted to the rim of the piston, and the outer edge is mounted to the body. The web has a generally U-shaped bend as viewed in axial cross-section, so that movement of the piston will cause it to lay against or be moved away from portions of the inner surface of the peripheral wall which surround the exit port or ports, thereby operating as a valve means for controlling flow through the exit ports.

An outlet check valve 50 is mounted to the body inside of the peripheral skirt. At its point of mounting there may be a structure such as a bead 51 to hold it. A plurality of slits 52 will be provided to divide the lower portion of the check valve into leaflets. This facilitates the opening and closing of the check valve. Preferably there will be a leaftlet for each exit port, as shown.

The outlet check valve, flapper valve, and the rolling diaphragm are all preferably made of silicone rubber. Very few substances stick readily to silicone rubber, and it is therefore unlikely to be affected by saliva, condensed vapors, and the like, which may be present to impede the function of the valve. This is true even if the moisture should freeze into ice. Silicone rubber keeps its flexibility at low temperatures and is in all ways a superior product for manufacture of these parts. Furthermore, the rolling operation of the diaphragm is noiseless and the flapping operation of the outlet check valve and of the flapper valve, being flexible, are similarly noiseless so that they do not cause distraction of the user.

Bias means 53 such as a weak spring tends to bias the piston toward its entended (inhaling) position. The strength of the spring will be determined by the other parameters of the piston and of the pressure differential caused by the breathing operation of the user.

The operation of the valve should be evident from the foregoing. During the inhaling operation as seen on the right hand side, the negative pressure caused by the inhaling movement of the user will cause (together with the bias spring) a raising of the piston and a lifting of the inlet flapper valves so as to permit breathing gas to enter the cavity and flow to the user. This flow is shown by arrow 55. When the user exhales, pressure in the cavity on the connector side of the valve will rise. The flapper valve will be pressed down to close the passages, and the piston will move down. This causes the rolling diaphragm to uncover the exit ports, whereas the inhaling sequence had caused it to close them. As the exit ports open, exhaling flow occurs as shown by arrow 56. This will cause the check valve to open and permit the flow. However, as soon as there is no positive pressure differential across the check valve it will return to the position shown on the right hand side of FIG. 1 and prevent backward of flow of gas, thereby protecting the user. The provision of a plurality of leaflets for each individual exit port provides greater reliability of the check valve operation.

This valve is elegantly simple in construction and provides substantial advantages of reliability and silence in its use.

This invention is not to be limited by the embodiment shown in the drawings and described in the description which is given by way of example and not of limitation, but only in accordance with the scope of the appended claims.

We claim:

1. A breathing valve for the selective entry of a gas to be breathed, and exit of exhaled gas, said valve comprising:
   a body having an axis, an internal cavity, a peripheral wall having an annular inner surface facing into said cavity, and an outer surface facing outside of said cavity, said wall having an exit port extending between said surfaces, said exit port where it intersects said surface being surrounded by portions of said surfaces, said inner surface having said axis as its center of curvature, said body having an inlet port and a connector port entering said cavity, said inlet port being adapted to be connected to a using device;
   a piston movably mounted in said cavity, centered on said axis, said piston having a first and a second side, said first side communicating with said inlet port, and said second side being communicable with said connector port, a passage extending between said sides, a seat encircling said passage on said second side, and an inlet flapper valve having a movable portion adapted to overlay and close said passage at said second side by bearing against said seat, and to be moved away from said seat to open the same;
   a central axial shaft extending into said cavity, a central spindle on said piston which is slidably fitted on said shaft, said flapper valve being mounted on said spindle;
   a peripheral rolling diaphragm having an inner and an outer concentric edge, and a flexible imperforate web between them, said inner edge being connected to said piston, and said outer edge being connected to said body adjacent to said exit port, whereby axial movement of said piston in one direction tends to lay part of said web against said inner surface and cover and close said exit port, and in an opposite direction to move away from said exit port and open the same, one side of said diaphragm being exposed to pressure from said inlet port, and the other side being exposed to pressure from said connector port and when and where it is adjacent to said exit port, there is is exposed to pressure in said exit port;
   an outlet check valve mounted to said body adjacent to said outer surface and adapted to be moved against said outer surface to close said exit port and away from it to open the same; and
   bias means biasing said piston in the direction tending to cause said rolling diaphragm to close said exhaust port.

2. A breathing valve according to claim 1 in which said flapper valve is disc-like, and has an outer annular portion adapted to make sealing contact with said seat, said seat encircling said axis.

3. A breathing valve according to claim 1 in which there is a plurality of angularly spaced-apart said exit ports, said outlet check valve comprising a plurality of leaflets.

4. A breathing valve according to claim 3 in which said flapper valve is disc-like, and has an outer annular portion adapted to make sealing contact with said seat, said seat encircling said axis.

5. A breathing valve according to claim 1 in which said flapper valve, said outlet check valve, and said diaphragm are made of silicone rubber.

6. A breathing valve according to claim 1 in which said seat is formed as a rim, and in which a plurality of spokes join said spindle and rim, and thereby form a plurality of said passages between them.

7. A breathing valve according to claim 6 in which said flapper valve is disc-like, and has an outer annular portion adapted to make sealing contact with said seat, said seat encircling said axis.

8. A breathing valve according to claim 1 in which said web has a U-shaped axial cross-section adjacent to its outer edge.

9. A breathing valve according to claim 8 in which a protective skirt overhanges at least the major portion of said outlet check valve.

10. A breathing valve according to claim 9 in which said flapper valve is disc-like, and has an outer annular portion adapted to make sealing contact with said seat, said seat encircling said axis.

11. A breathing valve according to claim 10 in which said there is a plurality of angularly spaced-apart said exit ports, said outlet check valve comprising a plurality of leaflets.

12. A breathing valve according to claim 11 in which said flapper valve, said outlet check valve, and said diaphragm are made of silicone rubber.

13. A breathing valve for the selective entry of a gas to be breathed, and exit of exhaled gas, said valve comprising:
 a body having an axis, an internal cavity, a peripheral wall having an annular inner surface facing into said cavity, and an outer surface facing outside of said cavity, said wall having an exit port extending between said surfaces, and said exit port where it intersects said surface being surrounded by portions of said surfaces, said inner surface having said axis as its center of curvature, said body having an inlet port and a connector port entering said cavity, said inlet port being adapted to be connected to a using device;
 a piston movably mounted in said cavity, centered on said axis, said piston having a first and a second side, said first side communicating with said inlet port, and said second side being communicable with said connector port, a passage extending between said sides, a seat encircling said passage on said second side, and an inlet flapper valve having a movable portion adapted to overlay and close said passage at said second side by bearing against said seat, and to be moved away from said seat to open the same;
 a central axial shaft extending into said cavity, a central spindle on said piston which is slidably fitted on said shaft, said flapper valve being mounted to said spindle;
 a peripheral rolling diaphragm having an inner and an outer concentric edge, and a flexible imperforate web between them, said inner edge being connected to said piston, and said outer edge being connected to said body adjacent to said exit port, whereby axial movement of said piston in one direction tends to lay part of said web against said inner surface and cover and close said exit port, and in an opposite direction to move away from said exit port and open the same, one side of said diaphragm being exposed to pressure from said inlet port, and the other side being exposed to pressure from said connector port and when and where it is adjacent to said exit port, there it is exposed to pressure in said exit port; and bias means biasing said piston in the direction tending to cause said rolling diaphragm to close said exhaust port.

14. A breathing valve according to claim 13 in which said flapper valve is disc-like, and has an outer annular portion adapted to make sealing contact with said seat, said seat encircling said axis.

15. A breathing valve according to claim 13 in which there is a plurality of angularly spaced-apart said exit ports, said outlet check valve comprising a plurality of leaflets.

* * * * *